United States Patent [19]

Iwuala

[11] Patent Number: 5,413,552
[45] Date of Patent: May 9, 1995

[54] ARM SLING WITH HUMERAL STABILIZER

[76] Inventor: Gloria D. Iwuala, 8918 Winding River, Houston, Tex. 77088

[21] Appl. No.: 254,521
[22] Filed: Jun. 6, 1994
[51] Int. Cl.⁶ ............................................. A61F 5/40
[52] U.S. Cl. .................................... 602/4; 602/20; 128/878
[58] Field of Search ................. 602/4, 5, 20, 62, 63, 602/61, 60; 128/881, 878, 876, 869, 846, 845, 878

[56] References Cited

U.S. PATENT DOCUMENTS

| | | | |
|---|---|---|---|
| 2,796,862 | 6/1957 | Borntraeger | 602/4 |
| 4,198,964 | 4/1980 | Honneffer . | |
| 4,220,149 | 9/1980 | Mims, Jr. | 602/4 |
| 4,355,635 | 9/1982 | Bihl | 128/94 |
| 4,372,301 | 2/1983 | Hubbard et al. | 602/4 |
| 4,550,869 | 11/1985 | Johnson | 602/20 |
| 4,564,008 | 1/1986 | Donahoo | 602/4 |
| 4,625,719 | 12/1986 | Chambers | 602/4 |
| 4,759,353 | 7/1988 | Melendez et al. | 602/4 |
| 4,834,082 | 5/1989 | Ghadiali | 602/4 |
| 4,901,713 | 2/1990 | Troeger | 602/4 |
| 4,947,870 | 8/1990 | Larcher | 128/876 |
| 5,086,762 | 2/1992 | Chu | 602/4 |
| 5,141,488 | 8/1992 | Schrader | 602/4 |
| 5,203,763 | 4/1993 | Lajiness-O'Neill | 602/4 |

Primary Examiner—Robert A. Hafer
Assistant Examiner—Michael O'Neill
Attorney, Agent, or Firm—Larry Mason Lee

[57] ABSTRACT

The present invention is an arm sling with humeral stabilizer which includes a shoulder strap anchorage which connects to a torso belt. A first strap is attached at one end to the wrist portion of a sling or arm cast, passes through a loop on the shoulder anchorage, and attaches to the elbow portion of the sling or cast. A second strap is adapted to connect at one end to a torso belt, pass through a loop on the shoulder anchorage, and connect at the strap's other end to the torso belt. The utilization of the shoulder anchorage arrangement causes the weight of the supported arm to be borne by the shoulder rather than the neck.

2 Claims, 2 Drawing Sheets

5,413,552

ARM SLING WITH HUMERAL STABILIZER

SUMMARY OF THE INVENTION a. Field of Invention

The present invention relates to the field of apparatus for supporting an injured arm.

More particularly, the present invention relates to apparatus for supporting an injured arm which further provides a humeral stabilizer.

Yet more particularly, the present invention relates to apparatus for supporting an injured arm which further provides a humeral stabilizer which yet further provides a shoulder strap anchorage which causes the weight of the supported arm to be borne by the shoulder rather than the neck.

b. Background of the Invention

Prior art in the field of apparatus for supporting an injured arm includes sling devices which provide humeral stabilization. However, difficulties have arisen in use of such sling devices in that such sling devices are supported by a strap across the shoulder opposite the injured arm, which strap asserts pressure against the neck and causes subsequent discomfort to the patient.

A substantial need exists for apparatus useful in supporting an injured arm which provide humeral stabilization.

An further need exists for such above-described apparatus which is supported by a strap across the shoulder opposite the injured arm and does not assert pressure against the neck and cause subsequent discomfort to the patient.

Accordingly, it is a primary object of this invention to provide apparatus useful in supporting an injured arm which provide humeral stabilization.

It is a further and final object of this invention to provide apparatus which is useful in supporting an injured arm and in providing humeral stabilization and which is supported by a strap across the shoulder opposite the injured arm which does not assert pressure against the neck and cause subsequent discomfort to the patient.

DESCRIPTION OF THE PREFERRED EMBODIMENT

Figure 1:
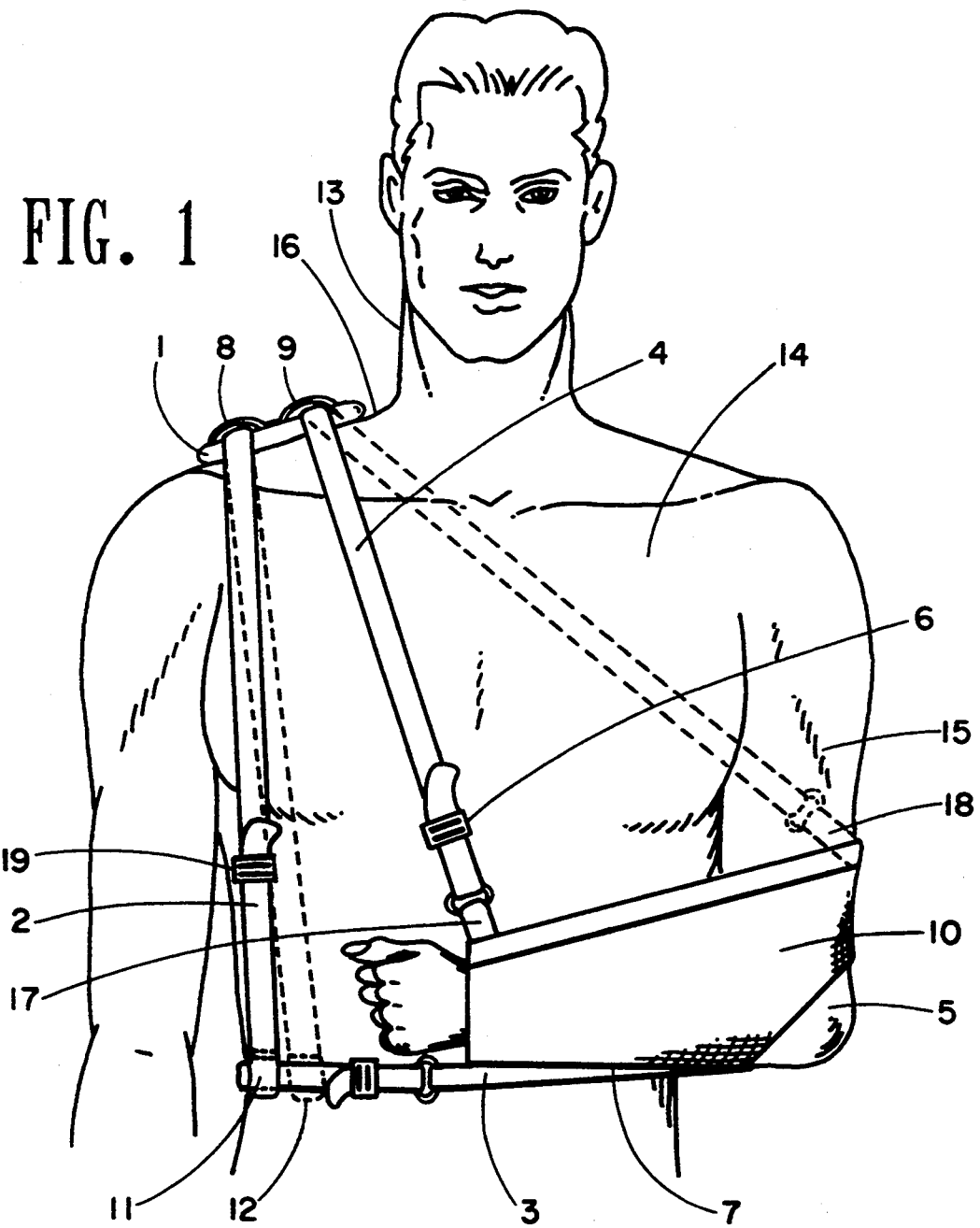
FIG. 1 is a frontal horizontal plane view of the instant invention on a patient, in position for use supporting an injured arm.
Figure 2:
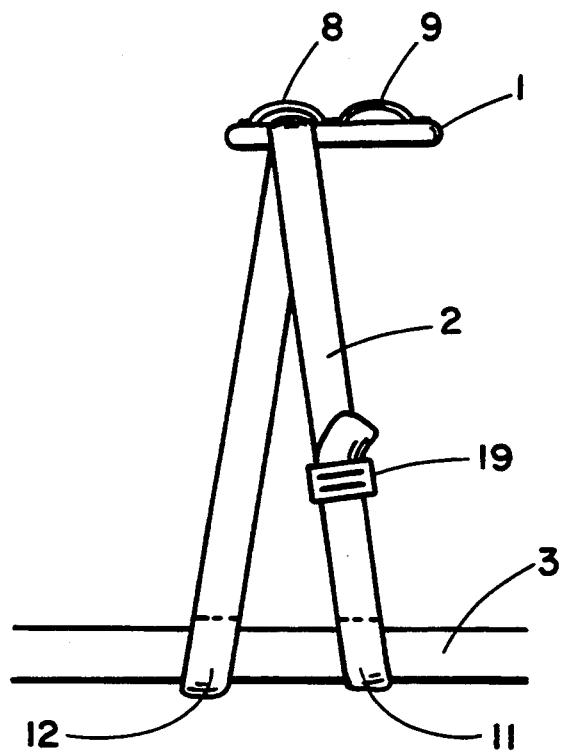
FIG. 2 is a horizontal plane view of the shoulder anchorage, shoulder anchorage strap, and a portion of the torso belt of the instant invention.
Figure 3:
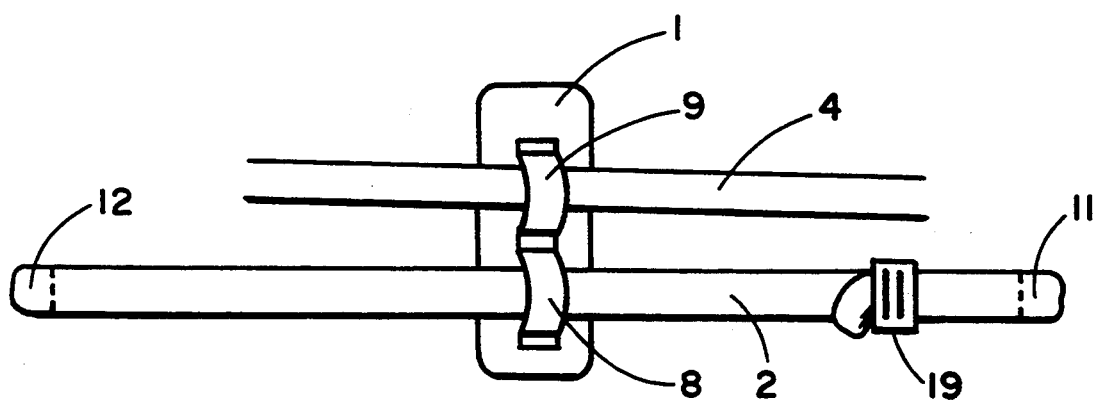
FIG. 3 is a vertical plane view of the shoulder anchorage with the shoulder anchorage strap and a portion of the sling support strap of the instant invention connected for use.

A standard (not the instant invention) sling for an injured arm (15) would provide only a sling support strap (4) which has connection (17) to the front of a pouch (10) in which the injured arm (15) rests, goes over the shoulder (16) opposite the injured arm (15), and has second connection (18) to the rear of the pouch (10). The front of the pouch (10) being deemed to be that portion of the pouch (10) from which the wrist and hand would, in use, extend; the rear of the pouch (10) being deemed to be that portion of the pouch (10) in which the elbow (5) of the injured arm (15) rests. The sling support strap (4) of a standard sling would usually provide a length adjustment means (6) to adjust the length of the sling support strap (4) in order to provide proper support to the pouch (10) and the injured arm (15) resting therein. The instant invention, as seen in the accompanying drawings, is a sling which provides support for a patient's (14) injured arm (15) in a pouch (10) while providing a padded shoulder anchorage (1) for the sling support strap (4) of the sling which shoulder anchorage (1) keeps the sling support strap (4) from asserting pressure on the patient's (14) neck (13). The instant invention provides, in addition to those above-stated components of a standard sling for an injured arm (15), a shoulder anchorage (1), a shoulder anchorage strap (2), and a torso belt (3). The shoulder anchorage strap (2) provides a length adjustment means (19) to adjust the length of the shoulder "anchorage strap (2). The torso belt (3) is worn around the upper waist or lower torso of the patient (14) and serves as a platform for the attachment of the shoulder anchorage strap's (2) slideable connections (11 and 12). The rear of the pouch (10) is open to permit the protrusion of the elbow (5) thereby cradling the elbow (5) and aligning the pouch (10)."

The sling support strap (4) of a standard sling, by virtue of the sling support strap's (4) angle from vertical across the back of a patient (14) when in use, produces both vertical and horizontal forces on the shoulder (16) of the patient (14). The horizontal forces on the shoulder (16) cause the sling support strap (4) to slide across the shoulder (16), moving toward and pressing upon the neck (13) of the patient (14). The pressing of the sling support strap (4) upon the neck (13) of the patient (14) can be, and often is, the source of considerable discomfort to the patient (14).

A substantial lessening of the discomfort to the patient (14) when wearing a sling can be achieved by providing a means to counteract the horizontal forces asserted on the shoulder (16) by the sling support strap (4). The instant invention provides a shoulder anchorage (1) which, in use, rests upon the patient's (14) shoulder (16), as a means of counteracting the horizontal forces asserted on the shoulder (16) by the sling support strap (4). The shoulder anchorage (1) provides, on its top side, two loops of material (8 and 9) through which the shoulder anchorage strap (2) and the sling support strap (4), respectively, are threaded. The bottom side, facing the shoulder (16) when in position for use, of the shoulder anchorage (1) should ideally provide a padded, smooth surface in order to cause minimal discomfort to the shoulder (16) of the patient (14), wearer. The shoulder anchorage strap (2), in use, has slideable connection (11) to the torso belt (3), goes over the shoulder (16) and through the loop (8) on the top of the shoulder anchorage (1), and has a second slideable connection (12) to the torso belt (3). The slideable connections (11 and 12) of the shoulder anchorage strap (2) to the torso belt (3) tend, in use, to slide toward one another whereby the shoulder anchorage strap (2) forms an angle from the vertical from the shoulder (16) to the patient's (14) torso beneath the arm opposite the injured arm (15) of the patient (14). The shoulder anchorage strap (2), through adjustment of its length with length adjustment means (19), can be tightened as necessary to provide the proper horizontal force opposing that horizontal force asserted on the shoulder (16) by the sling support strap (4). The sling support strap (4), in use, has connection (17) to the front of the pouch (10), goes over the shoulder (16) opposite the injured arm (15) and through the loop (9) on the top of the shoulder anchorage (1), and has a second connection (18) to the rear of the pouch (10).

The shoulder anchorage strap (2), in use and when connected as above-described, provides a means to counteract the horizontal forces asserted on the shoulder (16) by the sling support strap (4). The opposing horizontal forces produced by the shoulder anchorage strap (2) and the sling support strap (4) keep the shoulder anchorage (1) and thus the sling support strap (4) from moving toward the neck (13) of the patient (14) and thus relieve substantially the discomfort experienced by the patient (14) while wearing the sling for an injured arm (15).

The instant invention provides for a connection (7) from the pouch (10) to the torso belt (3). Such connection (7) extends along the lower length of the pouch (10) from front to rear. Further, the connection (7) prevents movement of the injured arm (15), while resting within the pouch (10), away from the torso of the patient (14) and "thereby provides humeral support. Connection (7) is made, in the preferred embodiment, by sewing the lower length of the pouch (10), from front to rear, to the torso belt (3)."

The instant invention may be used as support for either a right or a left injured arm (15) and thus may be considered a universal sling. In each case, right or a left injured arm (15), the shoulder anchorage (1) is placed upon the shoulder (16) opposite the injured arm (15) and the loop (9) closest to the neck (13) of the patient (14) is the loop through which the sling support strap (4) is fed, while the loop (8) farthest from the neck (13) of the patient (14) is the loop through which the shoulder anchorage strap (2) is fed.

This invention and its operation have been described in terms of a single preferred embodiment; however, numerous embodiments are possible without departing from the essential characteristics thereof. Accordingly, the description has been illustrative and not restrictive as the scope of the invention is defined by the appended claims, not by the description preceding them, and all changes and modifications that fall within the stated claims or form their functional equivalents are intended to be embraced by the claims.

I claim:

1. An improved sling for a patient's injured arm comprising:
   a pouch adapted to support said injured arm, the rear of said pouch providing an open end adapted to permit the protrusion of the elbow of said injured arm, and the front of said pouch providing an open end adapted to permit the protrusion of the hand and wrist of said injured arm;
   a shoulder anchorage pad which is adapted to rest on top of said patient's shoulder opposite said injured arm, and which provides a plurality of loops through which a plurality of straps are threaded;
   a sling support strap having two connection ends wherein the first end connection is connected to the front of said pouch, is adapted to be draped over said patient's shoulder opposite said injured arm, said sling support strap is threaded through one of said loops in said shoulder anchorage pad, and the second end connection is connected to the rear of said pouch
   a torso belt which is adapted to be worn around said patient's upper waist or torso, and is attached to said pouch along said pouches' bottom edge; and
   a shoulder anchorage strap having two slidable connection ends wherein the first slidable connection end is slidably connected to said torso belt and slides along a circumferential axis of said torso belt, is adapted to be draped over said patient's shoulder opposite said injured arm, said shoulder anchorage strap is threaded through one of said loops in said padded shoulder anchorage, and the second slidable connection end is slidably connected to said torso belt and slides along a circumferential axis of said torso belt.

2. The sling of claim 1 wherein
said shoulder anchorage is padded on its bottom side;
said shoulder anchorage provides a loop on its top side through which said sling support strap is threaded;
said shoulder anchorage provides a loop on its top side through which said shoulder anchorage strap is threaded;
said sling support strap provides a length adjustment means to adjust the length of said sling support strap; and
said shoulder anchorage strap provides a length adjustment means to adjust the length of said shoulder anchorage strap.

* * * * *